(12) United States Patent
Johansson et al.

(10) Patent No.: US 10,675,455 B2
(45) Date of Patent: *Jun. 9, 2020

(54) ORAL CARE IMPLEMENT WITH CONDUCTIVE PROTRUSIONS

(71) Applicant: Colgate-Palmolive Company, New York, NY (US)

(72) Inventors: Patrik Johansson, Hoboken, NJ (US); Harsh Mahendra Trivedi, Hillsborough, NJ (US); Douglas Hohlbein, Hopewell, NJ (US)

(73) Assignee: Colgate-Palmolive Company, New York, NY (US)

( * ) Notice: Subject to any disclaimer, the term of this patent is extended or adjusted under 35 U.S.C. 154(b) by 611 days.

This patent is subject to a terminal disclaimer.

(21) Appl. No.: 15/426,361

(22) Filed: Feb. 7, 2017

(65) Prior Publication Data

US 2017/0143957 A1    May 25, 2017

Related U.S. Application Data

(63) Continuation of application No. 14/885,502, filed on Oct. 16, 2015, now Pat. No. 9,597,496.

(51) Int. Cl.
*A61N 1/00* (2006.01)
*A61N 1/05* (2006.01)
(Continued)

(52) U.S. Cl.
CPC ........ *A61N 1/0548* (2013.01); *A46B 15/0022* (2013.01); *A61C 17/16* (2013.01); *A61C 17/222* (2013.01); *A61N 1/26* (2013.01); *A61N 1/322* (2013.01); *A61N 1/326* (2013.01); *C25B 1/26* (2013.01); *C25B 1/28* (2013.01); *C25B 1/285* (2013.01); *C25B 9/06* (2013.01); *A61N 1/205* (2013.01)

(58) Field of Classification Search
CPC ........ A61N 1/0548; A61N 1/205; A61N 1/26; A61N 1/322; A46B 15/0022; A61C 17/222

See application file for complete search history.

(56) References Cited

U.S. PATENT DOCUMENTS 3,520,297 A    7/1970    Bechtold
4,743,199 A    5/1988    Weber et al.
(Continued)

FOREIGN PATENT DOCUMENTS

CN    101355891    5/2011
WO    WO 2013/042307    3/2013

OTHER PUBLICATIONS

International Search Report and Written Opinion for priority application No. PCT/US2016/057028, dated Dec. 8, 2016. WO.

*Primary Examiner* — Lindsey G Wehrheim

(57) ABSTRACT

An oral care implement having conductive protrusions. In one embodiment, the oral care implement includes a handle and a head coupled to the handle. Furthermore, the oral care implement includes a power source. A plurality of conductive protrusions may be electrically coupled to the power source. The plurality of conductive protrusions may include a base proximate the head and a distal end spaced from the head. Furthermore, at least one of the conductive protrusions may taper from the base to the distal end.

16 Claims, 4 Drawing Sheets

(51) Int. Cl.
*A61N 1/32* (2006.01)
*A61N 1/26* (2006.01)
*A61C 17/22* (2006.01)
*C25B 1/26* (2006.01)
*C25B 9/06* (2006.01)
*C25B 1/28* (2006.01)
*A46B 15/00* (2006.01)
*A61C 17/16* (2006.01)
*A61N 1/20* (2006.01)

(56) References Cited

U.S. PATENT DOCUMENTS

| | | |
|---|---|---|
| 5,921,251 A | 7/1999 | Joshi |
| 7,775,795 B2 | 8/2010 | Khawaled et al. |
| 7,886,398 B2 | 2/2011 | Morita et al. |
| 2006/0070195 A1* | 4/2006 | Morita ............... A46B 15/0016 15/105 |
| 2007/0212665 A1 | 9/2007 | Jimenez et al. |
| 2011/0289699 A1* | 12/2011 | Schaefer ............ A46B 15/0002 15/4 |
| 2013/0071805 A1 | 3/2013 | Doll et al. |
| 2013/0071806 A1 | 3/2013 | Doll et al. |
| 2013/0071807 A1 | 3/2013 | Doll et al. |
| 2013/0072851 A1 | 3/2013 | Doll et al. |
| 2014/0106309 A1 | 4/2014 | Jimenez et al. |
| 2015/0074928 A1 | 3/2015 | Corbett et al. |
| 2015/0230593 A1 | 8/2015 | Doll et al. |

* cited by examiner

ORAL CARE IMPLEMENT WITH CONDUCTIVE PROTRUSIONS

CROSS-REFERENCE TO RELATED APPLICATIONS

The present application is a continuation of U.S. patent application Ser. No. 14/885,502, filed Oct. 16, 2015, now granted as U.S. Pat. No. 9,597,496, the entirety of which is incorporated herein by reference.

BACKGROUND

Various products and processes have been developed to improve and maintain oral health. For example, formulations such as mouthwashes, creams, pastes, salves, and the like, are known for reducing bacteria in the mouth and/or for treating conditions such as oral wounds and lesions. Conventionally, the formulations are applied to the teeth, gums and/or other areas of the oral cavity by rinsing, brushing, or otherwise. However, there is a need in the art for improved implements and methods for treating the oral cavity.

Accordingly, there is a need in the art for effective oral care devices. This disclosure is directed at overcoming one or more problems set forth above and/or other problems of the prior art.

BRIEF SUMMARY

This application describes improved oral care implements and methods for treating the oral cavity. In some embodiments, an oral care implement herein may be embodied as a self-contained device for at least partial placement in the oral cavity. The implement may include a housing, a power source, and a plurality of conductive protrusions depending from one or more surfaces of the housing. The conductive protrusions may act as electrodes to create an electrical field providing oral health benefits. In some implementations, the conductive protrusions may include positively charged and negatively charged protrusions. In other implementations, the conductive protrusions may be similarly charged, and a separate conductive element may be provided and charged oppositely from the protrusions.

In other implementations, methods for killing bacteria, for treating oral wounds and/or for providing other oral benefits are provided. For instance, methods according to this disclosure may include activating the power source on an implement such as described above and contacting the implement with a surface in the oral cavity, such as a soft-tissue surface. Current to the protrusions from the power source may also be controlled, for example, such as to provide a pulsed electrical stimulation.

In one aspect, the invention may be an oral care implement comprising: a handle; a head coupled to the handle; a power source; a plurality of conductive protrusions electrically connected to the power source and extending from the head, each of the conductive protrusions comprising a base that is proximate to the head and a distal end opposite the base that is spaced from the head; and wherein at least one of the conductive protrusions tapers from the base to the distal end thereof.

In another aspect, the invention may be an oral care implement comprising: a handle; a head coupled to the handle and comprising a cavity and an outer surface; a power source located in the cavity, a first electrical pathway coupled to a positive terminal of the power source and a second electrical pathway coupled to a negative terminal of the power source; a first set of conductive protrusions coupled to the first electrical pathway and extending from the outer surface of the head; and a second set of conductive protrusions coupled to the second electrical pathway and extending from the outer surface of the head.

In still another aspect, the invention may be an oral care implement comprising: a body comprising a handle and a head; a power source; a plurality of conductive protrusions electrically connected to the power source and depending from a surface of the body, the plurality of conductive protrusions generating one or more electric fields; control circuitry operably coupled to the power source, wherein the control circuitry is configured to pulse at least one of the one or more electric fields.

In aspects of this disclosure, an oral care implement includes a housing configured for insertion into an oral cavity; a power source disposed in the housing; a first array of positively charged conductive protrusions electrically connected to the power source, each of the positively charged conductive protrusions depending from a surface of the housing; and a second array of negatively charged conductive protrusions electrically connected to the power source, each of the negatively charged conductive protrusions depending from the surface of the housing, wherein an electrical field is generated between the first array of positively charged conductive protrusions and the second array of negatively charged conductive protrusions.

In one or more additional aspects, in an oral care implement as described in any of the preceding paragraphs, the first array and the second array may be configured such that respective of the positively charged conductive protrusions are immediately adjacent to at least one of the second conductive protrusions.

In one or more additional aspects, in an oral care implement as described in any of the preceding paragraphs, the first array comprises between about two and about 100 positively charged conductive protrusions per square centimeter and the second array comprises between about two and about 100 negatively charged conductive protrusions per square centimeter.

In one or more additional aspects, in an oral care implement as described in any of the preceding paragraphs, control circuitry selectively applies current to at least one of the first array and the second array from the power source.

In one or more additional aspects, in an oral care implement as described in any of the preceding paragraphs, each of the positively charged conductive protrusions has a height from a base proximate the surface to a distal end of up to about 5 millimeters.

In one or more additional aspects, in an oral care implement as described in any of the preceding paragraphs, each of the negatively charged conductive protrusions has a height from a base proximate the surface to a distal end of up to about 5 millimeters.

In one or more additional aspects, in an oral care implement as described in any of the preceding paragraphs, each of the positively charged conductive protrusions is spaced no more than about 5 millimeters from a negatively charged conductive protrusion.

In one or more additional aspects, in an oral care implement as described in any of the preceding paragraphs, the first array has a surface area of up to about 1 $cm^2$ and the second array has a surface area of up to about 1 $cm^2$.

In one or more additional aspects, in an oral care implement as described in any of the preceding paragraphs, the first array has a surface area of up to about 6 $cm^2$ and the second array has a surface area of up to about 6 $cm^2$.

In one or more additional aspects, in an oral care implement as described in any of the preceding paragraphs, the power source may be disposed in the housing.

In one or more additional aspects, a method of treating the oral cavity may include providing the oral care implement of any of the preceding paragraphs and generating an electrical field by supplying power from the power source to positively charge the first array and/or negatively charge the second array.

In other aspects of this disclosure, an oral care implement includes a handle; a head disposed at a distal end of the handle; a power source; a plurality of positively charged conductive protrusions depending from a surface of the head and electrically connected to the power source; and a plurality of negatively charged conductive protrusions depending from the surface of the head and electrically connected to the power source.

In one or more additional aspects, in an oral care implement as described in the preceding paragraph, the power source is disposed in the head or in the handle.

In one or more additional aspects, in an oral care implement as described in any of the preceding two paragraphs, a distance between one of the positively charged conductive protrusions and one of the negatively charged conductive protrusions is up to about 5 millimeters.

In one or more additional aspects, in an oral care implement as described in any of the preceding three paragraphs, a distance between one of the positively charged conductive protrusions and one of the negatively charged conductive protrusions is up to about 1 millimeter.

In one or more additional aspects, in an oral care implement as described in any of the preceding four paragraphs, a distance between one of the positively charged conductive protrusions and one of the negatively charged conductive protrusions is not more than about 0.1 millimeter.

In one or more additional aspects, in an oral care implement as described in any of the preceding five paragraphs, each of the positively charged conductive protrusions and each of the negatively charged conductive protrusion extends from a base proximate the surface of the housing to a distal end.

In one or more additional aspects, in an oral care implement as described in the preceding paragraph, at least one of the positively charged conductive protrusions and at least one of the negatively charged conductive protrusions tapers from the base proximate the surface of the housing to the distal end.

In one or more additional aspects, in an oral care implement as described in any of the preceding two paragraphs, the distance between the base and the distal end is no more than about 5 millimeters.

In one or more additional aspects, in an oral care implement as described in any of the preceding three paragraphs, a distance between the base and the distal end is no more than about 1 millimeter.

In one or more additional aspects, in an oral care implement as described in any of the preceding four paragraphs, a distance between the base and the distal end is no more than about 0.1 millimeter.

In one or more additional aspects, a method of treating the oral cavity may include providing the oral care implement of any of the preceding ten paragraphs and generating an electrical field by supplying power from the power source to positively charge the first array and/or negatively charge the second array.

In other aspects of this disclosure, an oral care device includes a housing configured for insertion into an oral cavity; a power source; and a plurality of conductive protrusions electrically connected to the power source and depending from a surface of the housing.

In one or more additional aspects, in an oral care implement as described in the preceding paragraph, each of the conductive protrusions extends from a base proximate the surface of the housing to a distal end.

In one or more additional aspects, in an oral care implement as described in the preceding paragraph, each of the conductive protrusions tapers from the base proximate the surface of the housing to the distal end.

In one or more additional aspects, in an oral care implement as described in any of the preceding two paragraphs, a distance between the base and the distal end is less than about 5 millimeters.

In one or more additional aspects, in an oral care implement as described in any of the preceding three paragraphs, a distance between the base and the distal end is less than about 1 millimeter.

In one or more additional aspects, in an oral care implement as described in any of the preceding four paragraphs, a distance between the base and the distal end is less than about 0.1 millimeter.

In one or more additional aspects, in an oral care implement as described in any of the preceding six paragraphs, a first of the plurality of conductive protrusions is positively charged and a second of the plurality of conductive protrusions is negatively charged.

In one or more additional aspects, in an oral care implement as described in the preceding paragraph, the first of the plurality of conductive protrusions is spaced from the second of the plurality of conductive protrusions by a distance of no more than about 5 millimeters.

In one or more additional aspects, in an oral care implement as described in any of the preceding two paragraphs, the first of the plurality of conductive protrusions is spaced from the second of the plurality of conductive protrusions by a distance of no more than about 1 millimeter.

In one or more additional aspects, in an oral care implement as described in any of the preceding three paragraphs, the first of the plurality of conductive protrusions is spaced from the second of the plurality of conductive protrusions by a distance of no more than about 0.1 millimeter.

In one or more additional aspects, in an oral care implement as described in any of the preceding six paragraphs, the plurality of conductive protrusions comprises a first plurality of positively charged conductive protrusions and a second plurality of negatively charged conductive protrusions.

In one or more additional aspects, in an oral care implement as described in any of the preceding paragraphs, a conductive element is disposed on the housing, wherein the plurality of conductive protrusions are one of positively charged and negatively charged and the conductive element is the other of positively charged and negatively charged.

In one or more additional aspects, in an oral care implement as described in the preceding paragraph, the conductive element is electrically connected to the power source.

In one or more additional aspects, in an oral care implement as described in any of the preceding thirteen paragraphs, the plurality of conductive protrusions are made of one or more of steel, nickel, zinc, copper, titanium dioxide, and combinations thereof.

In one or more additional aspects, a method of treating the oral cavity may include providing the oral care device of any of the preceding fourteen paragraphs and generating an electrical field by supplying power from the power source to positively charge the first array and/or negatively charge the second array.

Further areas of applicability of the present disclosure will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the preferred embodiments is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

This disclosure relates generally to oral care implements, and more particularly to oral care implements capable of being partially or completely placed within the oral cavity to provide a benefit to the oral cavity. Although certain embodiments and benefits will be described, other implementations, modifications, and/or benefits will be appreciated by those having ordinary skill in the art, with the benefit of this disclosure. For example, the following detailed description may generally refer to embodiments of the inventive implements in the context of a toothbrush, but the disclosure is not limited to toothbrushes; other oral care implements may also incorporate features of this disclosure. By way of non-limiting example, embodiments of this disclosure may not include bristles. Moreover, mouth guard-type oral care implements, which do not include a handle (or bristles), are known, and aspects of this disclosure may be incorporated into such an implement.

Figure 1:
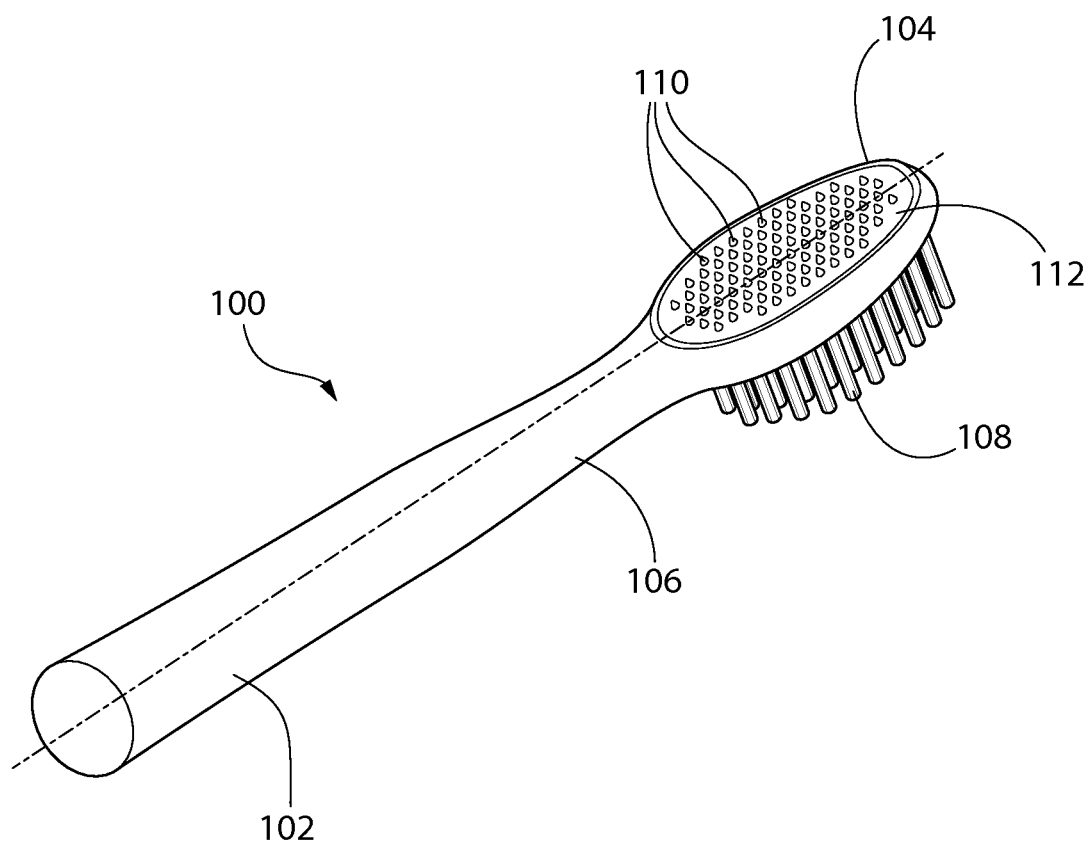
FIG. 1 is a perspective view of an oral care implement according to an example implementation of this disclosure.

FIG. 1 illustrates an oral care implement 100 according to embodiments of this disclosure. The oral care implement 100 is embodied as a toothbrush and generally includes a handle 102, a head 104 disposed at the distal end of the handle 102, and a neck portion 106 generally disposed between the handle 102 and the head 104. As illustrated, the handle has a generally elongate shape, along a longitudinal axis. This disclosure is not limited to the shape and/or size of the toothbrush illustrated in FIG. 1. In alternative implementations, one or more of the handle 102, head 104, and/or neck 106 may have different shapes, sizes, orientations, and/or the like. Additional features may also be incorporated into the toothbrush or disposed on the toothbrush.

The oral care implement also includes a plurality of bristles 108 depending from a front, bristle surface. The bristles 108 may be formed as bristle tufts. The tufts may be formed with bristles of the same or different bristle materials (such as nylon bristles, spiral bristles, rubber bristles, etc.). Moreover, while the bristles may be arranged so that they are generally perpendicular to a bottom surface of the head 104, some or all of the tooth cleaning elements may be angled at various angles with respect to the bottom surface. When bristle tufts are provided, it may be possible to select the combination of bristle configurations, bristle materials and/or bristle orientations to achieve specific intended results and operational characteristics, thus maximizing and enhancing cleaning, tooth polishing, tooth whitening, massaging, stimulation, and the like.

The bristles 108 may be attached to the head 104 by any conventional method. In certain embodiments, the bristles may be secured to a head plate having a plurality of holes formed therethrough, and the bristles may be mounted to the head plate within the holes. This type of technique for mounting the bristles to a head plate is generally known as anchor free tufting (AFT). In AFT a head plate or membrane is created and the tooth cleaning elements (such as bristles, elastomeric elements, and combinations thereof) are positioned into the head plate so as to extend through the holes of the head plate. The free ends of the tooth cleaning elements on one side of the head plate perform the cleaning function. The ends of the tooth cleaning elements on the other side of the head plate are melted together by heat to be anchored in place. As the tooth cleaning elements are melted together, a melt matte is formed, which is a layer of plastic formed from the collective ends of the tooth cleaning elements that connects the tooth cleaning elements to one another on one side of the head plate and prevents the tooth cleaning elements from being pulled through the tuft holes.

In some conventional designs, such as some conventional manual toothbrushes, after the tooth cleaning elements are secured to the head plate, the head plate may be secured to the head 104, such as by ultrasonic welding. When the head plate is coupled to the head 104, the melt matte is located between a lower surface of the head plate and a floor of a basin or cavity of the head 104 in which the head plate is disposed. The melt matte, which is coupled directly to and in fact forms a part of the tooth cleaning elements, prevents the tooth cleaning elements from being pulled through the holes in the head plate thus ensuring that the tooth cleaning elements remain attached to the head plate during use of the oral care implement.

In another embodiment, the tooth cleaning elements may be connected to a head plate or membrane using a technique known in the art as AMR. In this technique, a head plate is provided and the bristles are inserted into holes in the head plate so that free/cleaning ends of the bristles extend from the front surface of the head plate and bottom ends of the bristles are adjacent to the rear surface of the head plate. After the bristles are inserted into the holes in the head plate, the bottom ends of the bristles are melted together by applying heat thereto, thereby forming a melt matte at the rear surface of the head plate. The melt matte is a thin layer of plastic that is formed by melting the bottom ends of the bristles so that the bottom ends of the bristles transition into a liquid, at which point the liquid of the bottom ends of the bristles combine together into a single layer of liquid plastic that at least partially covers the rear surface of the head plate.

After the heat is no longer applied, the melted bottom ends of the bristles solidify/harden to form the melt matte/thin layer of plastic. In some conventional applications, after formation of the melt matte, a tissue cleaner is injection molded onto the rear surface of the head plate, thereby trapping the melt matte between the tissue cleaner and the rear surface of the head plate. Other structures may be coupled to the rear surface of the head plate to trap the melt matte between the rear surface of the head plate and such structure without the structure necessarily being a tissue cleaner. For example, in embodiments of this disclosure, a structure covering the melt matte may be a plastic material that is used to form a smooth rear surface of the head, or the like. In still other embodiments, the structure can be molded onto the rear surface of the head plate or snap-fit (or other mechanical coupling) to the rear surface of the head plate as desired.

Of course, techniques other than AFT and AMR can be used for mounting bristles, such as widely known and used stapling/anchoring techniques or the like. In such embodiments the bristles 108 may be coupled directly to the head. Furthermore, in a modified version of the AFT process discussed above, the head plate may be formed by positioning the bristles and/or other tooth cleaning elements within a mold, and then molding the head plate around the tooth cleaning elements via an injection molding process. However, it should be appreciated that certain of the bristle tufts disclosed herein may not be adequately secured to the head using staple techniques, and one of AFT or AMR may therefore be preferred for securing such bristle tufts.

Moreover, in certain embodiments, the invention can be practiced with various combinations of stapled, IMT, AMR, or AFT cleaning elements. Alternatively, the tooth cleaning elements could be mounted to tuft blocks or sections by extending through suitable openings in the tuft blocks so that the base of the tooth cleaning elements is mounted within or below the tuft block. In still other embodiments, likely in which the tooth cleaning elements are not bristles, the tooth cleaning elements may be molded integrally with the head.

As illustrated, the oral care implement 100 also includes a plurality of conductive protrusions 110. The conductive protrusions are formed on or otherwise extend relative to a surface of the head 104. As illustrated, the conductive protrusions 110 extend from a back surface 112 of the head 104, which is a surface opposite the bristles 108. Although the conductive protrusions 110 are illustrated as only protruding from the back surface 112, in some embodiments, the protrusions 110 may alternatively or additionally protrude from other surfaces of the head 104 and/or the neck 106. Without limitation, the protrusions 110 may also or alternatively protrude from the same surface of the head 104 as the bristles 108.

The conductive protrusions 110 may be formed as nubs or posts that extend a distance from the back surface 112. The conductive protrusions 110 are electrically conductive and act as electrodes in some embodiments. For instance, the conductive protrusions 110 may be positively or negatively charged depending upon an electrical current applied thereto. As will be described in more detail below, in some embodiments, some of the conductive protrusions 110 are positively charged and other of the conductive protrusions 110 are negatively charged. Accordingly, electrical fields are generated between the positively and negatively charged protrusions. This electrical field may be beneficial to oral health.

The conductive protrusions 110 may be attached to the head 104, or may protrude from a space inside the head 104 through the back surface 112 to extend from the back surface 112. In implementations, the conductive protrusions 110 may be formed of any conductive or semi-conductive material, including, but not limited to, steel, nickel, zinc, copper, titanium dioxide, and/or combinations thereof.

The conductive protrusions 110 are illustrated as each having substantially the same shape. Specifically, each of the conductive protrusions 110 is illustrated as tapering from a base proximate the back surface 112 of the head 104 to a distal end spaced from the base and the back surface 112. The distal end of each of the protrusions is illustrated as a point, such that the conductive protrusions 110 have a triangular cross-section. This disclosure is not limited to that shape. In other embodiments, the distal end of the protrusions 110 may be chamfered, radiused, flat, or the like. Moreover, the conductive protrusions 110 may include more or less taper than illustrated. In still other embodiments, the protrusions 110 may have no taper at all. More specifically, the surface area parallel to the plane of the back surface 112 of the protrusions 110 may be the same proximate the base of the protrusion and the distal end of the protrusion. As will be appreciated by those having ordinary skill in the art with the benefit of this disclosure, a number of configurations for the protrusions could be used. Moreover, it is not necessary that each of the protrusions be identically configured. Protrusions of different shapes may be included in the same oral care implement 100.

In addition to varying the shape of the conductive protrusions 110, the size of those protrusions also may be varied. In some implementations, the protrusions may extend up to about 5 mm from the back surface 112. In other embodiments, the protrusions 110 may extend up to about 1 mm from the back surface 112, and in still other embodiments, the protrusions 110 may extend up to about 0.1 mm from the back surface 112. In still other applications, the height of the protrusions 110 may be sub-micron. A two-dimensional surface area proximate the base of the protrusion 110 also may vary, e.g., depending upon the application, the manufacturing technique used to form the protrusions 110, or the like. Without limitation, a footprint of the protrusions 110, measured proximate the base of the protrusions 110, may range from about 1 square-micrometer to about 1 square centimeter. The height and size of the footprint of the protrusions may also be related.

Not only may the size and shape of each of the conductive protrusions 110 vary, but the spacing between adjacent of the protrusions 110 also may vary. As will be described in more detail below, the protrusions 110 may be charged to create an electrical field between the protrusions 110. Spacing between the protrusions 110 may have an influence on the strength of the electrical field, and thus may vary depending upon the desired application. In some embodiments, the protrusions 110 may be spaced relative to each other by no more than about 5 mm. In other embodiments, the protrusions 110 may be spaced from each other no more than about 1 mm, and in still other embodiments, the protrusions 110 may be spaced relative to each other by no more than about 0.1 mm. In still other embodiments, spacing between the protrusions 110 may be no more than about one micrometer. The spacing of the protrusions may also be related to the surface area and/or height of the protrusions 110.

Figure 2A:
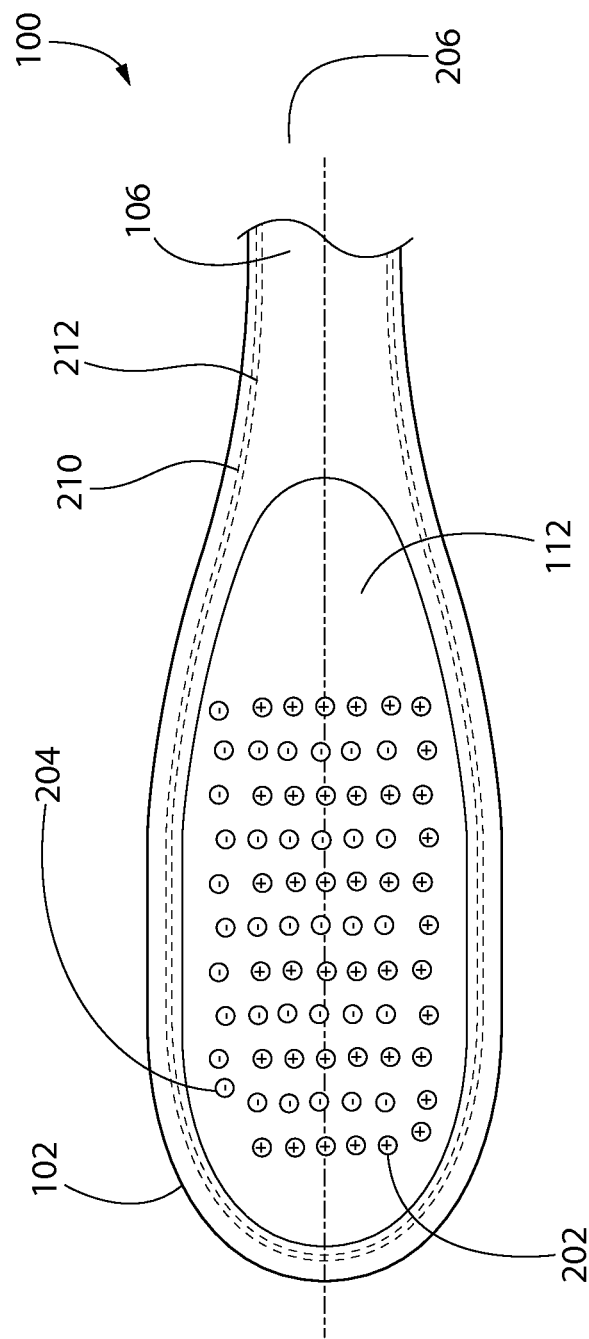
FIG. 2A is a plan top view of the oral care implement illustrated in FIG. 1, according to an example implementation of this disclosure.
Figure 2B:
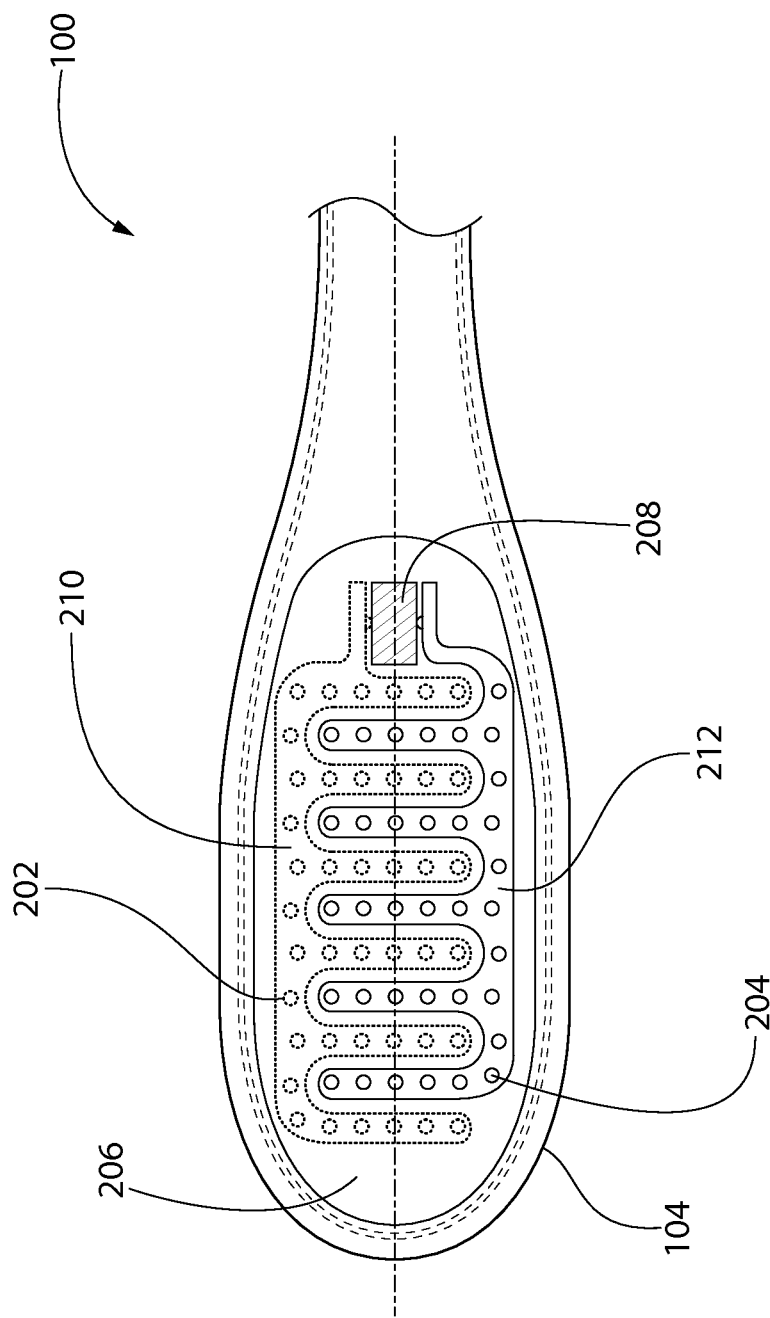
FIG. 2B is a plan bottom view of the oral care implement illustrated in FIG. 1 with the brushes and associated support removed, according to an example implementation of this disclosure.

FIGS. 2A and 2B illustrate additional details of the implement 100. Specifically, FIG. 2A is a plan view of the head 104 of the oral care implement 100 viewed normal to the back surface 112, and FIG. 2B is a plan view of the head 104 of the oral care implement 100 viewed normal to the front surface (from which the bristles protrude) with the bristles removed for clarity. In these figures, several of the conductive protrusions 110 are indicated (with a "+" symbol) as positively-charged protrusions 202 and several of the conductive protrusions 110 are indicated (with a "−" symbol) as negatively-charged protrusions 204. Together, the positively-charged protrusions 202 form an array or arrangement of positively-charged protrusions 202 and the negatively-charged protrusions 204 form an array or arrangement of negatively-charged protrusions.

As illustrated best in FIG. 2B, the head 104 provides a housing, defining a cavity 206 in which components of the implement 100 are contained. For example, a power source 208 is illustrated as being contained in the cavity 206 as well as a first electrical pathway 210 and a second electrical pathway 212. The first electrical pathway 210 is disposed to connect the positively-charged protrusions 202 to each other and to the power source 208. The second electrical pathway 212 is disposed to connect the negatively-charged protrusions 204 to each other and to the power source 208.

Although the conductive protrusions 110 are illustrated as positively-charged or negatively-charged, the polarity of the protrusions may be changed. For example, the illustrated positively-charged protrusions 202 may be negatively charged and the illustrated negatively-charged protrusions 204 may instead be positively charged. Moreover, in some implementations, for example, when the power source 208 is an alternating-current power source, the polarity may change as the current alternates. Of importance in some embodiments is that an electrical field may be generated between oppositely-charged protrusions 110.

In the arrangement illustrated in FIGS. 2A and 2B, the array of positively-charged protrusions 202 is complimentary to the array of negatively-charged protrusions 204 such that each of the positively-charged protrusions 202 is adjacent to at least one of the negatively-charged protrusions 204 in at least one radial direction. Such an arrangement allows for a flow of electrons from the positively charged protrusion 202 to the negatively charged protrusion 204, thereby forming the electrical field. This disclosure is not limited to the arrays illustrated in FIGS. 2A and 2B. In other embodiments, alternating rows of positively-charged and negatively-charged protrusions 110 may be provided. The rows may extend generally along the axial direction of the implement 100, or at any angle relative to the axial direction. In other embodiments, positively-charged protrusions 202 and negatively-charged protrusions 204 may alternate.

The Figures illustrate more positively-charged protrusions 202 than negatively-charged protrusions 204. In other embodiments, the negatively charged protrusions 204 may outnumber the positively-charged protrusions 202. In still other embodiments, the number of positively-charged protrusions 202 and negatively-charged protrusions 202 may be the same. Generally, any arrangement in which one or more electrical fields can be generated between protrusions may be used.

In some embodiments, it may be desirable that each array of protrusions covers a surface area up to about 1 cm$^2$, regardless of the size, shape, and/or number of protrusions actually present in the respective array. In other embodiments, each array may define a surface area of up to about 6 cm$^2$, regardless of the size, shape, and/or number of protrusions actually present. The number of protrusions also may vary for each array, depending for example, on size, spacing, total surface area, and the like. In some examples, each of the protrusions may have a footprint ranging from about 0.01 cm$^2$ to about 0.25 cm$^2$. Moreover, the protrusions may number from about 2 to about 100 protrusions per cm$^2$, although more or fewer protrusions could be used in some instances.

As noted above, in operation, the power source supplies current to positively charge the positively-charged protrusions 202 and negatively charge the negatively-charged protrusions 204. The result is a number of electrical fields formed between and around pairs of positively- and negatively-charged protrusions. The electrical fields may be used in the oral cavity for a number of benefits. For instance, pulsed electrical stimulation using the implement 100 may have an anti-microbial effect. Moreover, the benefit may be field-dependent. For example, in some instances, low-voltage pulsed current can provide an antimicrobial effect on at least three gram-negative organisms (*Escherichia coli*, *Pseudomonas aeruginosa*, and *Klebsiella pneumonia*) and at least three gram-positive organisms (*Staphylococcus aureus*, *Staphylococcus epidermidis*, and *Escherichia faecium*). In addition, direct current in the micro-amp range may have an anti-microbial effect on *Pseudomonas aeruginosa*, *Staphylococcus aureus*, and *Staphylococcus epidermidis*. Because in some implementations the device is intended to generate a field in an oral cavity, the strength of the field will be such that there is no adverse effect on the oral cavity or the patient. For example, the power source may supply power on the order of about one microvolt, and up to about six volts. Current through the arrays may range from about 0.1 micro-Amp to about 100 milli-Amps.

The implement 100 may have additional benefits. For example, electrical stimulation may have beneficial wound healing and pain management benefits. Placing the protrusions on or near an effected region in the oral cavity could deliver much needed relief to some ailments. The relief and other benefits from implementations of this disclosure may be as a rest of the electrical field and/or direct contact by the protrusions 110. In other implementations, the implement 100 may have a rejuvenating effect. For example, the electrical fields and stimulation by the protrusions may heal, rejuvenate, and/or treat bacterial colonies in the tongue and/or oral soft tissue, which could curb dry mouth and/or improve bad breath. Moreover, the implement 100 may disrupt the overall charge of the surface of oral soft tissue. Disruption of ionic, van der Waals, and/or London dispersion charges may promote dissociation of proteins and bacteria from the soft tissue. This process may also enhance or recover sensory receptors giving rise to an increased sensitivity toward food and/or oral care products.

Moreover, because the protrusions extend from the surface of the implement 100, they can be brought into direct physical contact with tissue in the oral cavity. This contact may provide a stimulating effect, such as a massaging effect, even in the absence of the electrical field.

The implement 100 may also be used with an activating agent or substance. The activating agent may be administered to the oral cavity separately, with the electrical field of the implement 100 acting on the activating agent, e.g., to provide an electrochemical benefit. The active substance or active agent may comprise a gel or paste containing a soluble and orally acceptable sulfate in a buffered, electrically conductive medium to the teeth or otherwise in the oral cavity and the device 100 activates the sulfate in the gel or paste to form persulfate. For example, in some embodiments, an effective amount of an oral care composition comprising an orally acceptable sulfate and/or bisulfate, e.g., potassium bisulfate ($KHSO_4$), in a buffered, electrically conductive medium may be applied to the teeth, and (just before or during application) the composition is exposed to an electric potential so as to facilitate in situ production of persulfate ($S_2O_8^{2-}$), e.g., potassium persulfate ($K_2S_2O_8$).

As used herein, the term "sulfate" refers to a salt or mixture of salts formed or capable of being formed by reaction of sulfuric acid with a base. The term therefore includes bisulfate salts. The term also includes monoperoxysulfate. In aqueous solutions, there may be an equilibrium between the fully deprotonated ion (sulfate or $SO_4^{2-}$) and the partially deprotonated ion (bisulfate or $HSO_4^-$), and both of these ions are capable of forming persulfate when exposed to an electrical potential in an aqueous medium. "Orally acceptable sulfate" refers to sulfates (including bisulfates) which are not toxic or harmful when administered as a component of an oral care product, at relevant concentrations, e.g., 10% or less. "Soluble sulfate" refers to sulfate salts (including bisulfates) which are soluble in aqueous solution at room temperature, e.g., having a solubility of at least 10 g per 100 mL water at 25° C. The term "soluble and orally acceptable sulfate" thus encompasses, for example, compounds such as $NaHSO_4$, $KHSO_4$, $(NH_4)HSO_4$, $Mg(HSO_4)_2$, $Na_2SO_4$, $K_2SO_4$, $(NH_4)_2SO_4$, and $MgSO_4$.

Sulfates are one type of inert salts that can be activated by the electrical field in embodiments of this disclosure, e.g., to provide a whitening, anti-bacterial, or other benefit. Other types of inert salts may include chlorides, for example, which may be activated to form hyper chlorites; phosphates, which may be activated to form peroxydiphosphates, peroxomonophosphates or peroxomonphosphoric acid; or carbonates, which may be activated to form peroxydicarbonate. Moreover, salts of peroxymonosulfuric acid, such as potassium peroxymonosulfate, may be oxidizing agents that can be activated by an electrical field to form powerful whitening agents.

As noted above, the activating agent may be placed in the oral cavity prior to insertion of the implement 100. In other embodiments, the activating agent may be provided on the oral care implement 100. For example, the activating agent may be provided as a gel, paste or other formulation on the head 104. A protective covering (not shown) such as a wrapper, barrier layer, or the like, may also be provided over the activating agent, e.g., to shield the activating agent. The covering may be intended to be removed prior to use. In other implementations, the barrier may dissolve in the mouth, and thus may not require removal.

The implement 100 may include additional features. For example, although not illustrated, a power switch, button, or other feature may be disposed on the device to allow a user to activate the power source. The power button may be disposed on the handle 102, for example, and electrically connected to the power source, e.g., via leads (not shown). The leads may be disposed in the handle and extend through the neck in such an embodiment.

Other interactive features also may be provided on the implement. For example, a switch, selector, toggle, or similar control may be provided that allows a user to select a mode for the implement 100. For example, the bristles 108 may be powered, and the user may be able to choose a brushing mode (powering the bristles), a cleaning mode (powering the conductive protrusions), or a mode that powers both the bristles and the protrusions. Regardless of whether the bristles are included or powered, a control may also enable a user to select between different modes for powering the conductive protrusions. For example, killing bacteria may be accomplished using a first mode, while healing a sore in the mouth may occur in a second mode.

The implement 100 may also include control circuitry for controlling power from the power source. For example, the control circuitry may be provided to pulse the electrical fields. For example, as noted above, low voltage, pulsed electrical fields may have beneficial anti-bacterial effects. Different circuitry or controls may be provided for different applications, as well. The control circuitry may also include timing capabilities, e.g., to automatically turn off the electrical field after a certain time.

Figure 3:
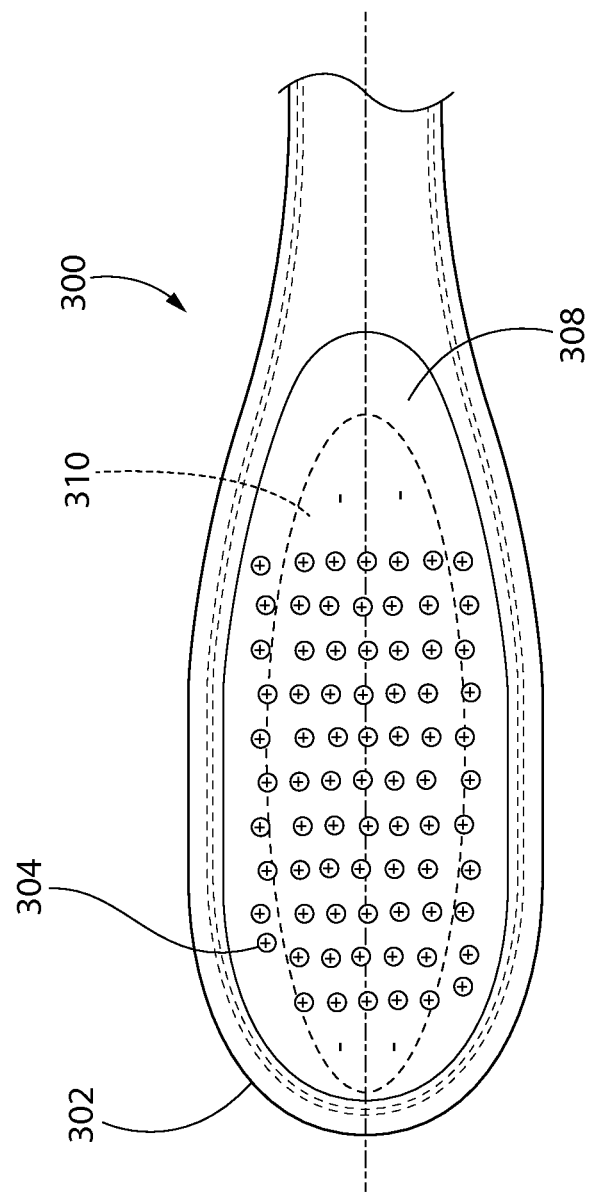
FIG. 3 is a plan view of an oral care implement according to another example implementation of this disclosure.

FIG. 3 illustrates another example of an oral care implement 300 according to another embodiment of this disclosure. The implement 300 generally includes a housing 302 sized for at least partial insertion into the oral cavity. The housing 302 is illustrated as a toothbrush head, which may be disposed at a distal end of a handle (not shown). In other implementations, the housing may be other than a toothbrush. For example, the housing may be adapted for mounting or otherwise retaining on a user's fingertip, for insertion into the oral cavity. This disclosure is not limited to the shape and/or size of the element 300 illustrated in FIG. 3. In alternative implementations, the housing 302 may have different shapes, sizes, orientations, and/or the like. Additional features may also be incorporated into the implement or disposed on the implement. For example, although not illustrated, the implement 300 may include bristles or other tooth cleaning elements, as in the implement 100.

The implement 300 includes a plurality of conductive protrusions 304 extending from a surface 306 of the implement. The conductive protrusions 304 may be formed in an array and have some or all of the same features and/or characteristics as the conductive protrusions 110 described above, which will not be discussed again here in detail. The surface 308 may be substantially planar, contoured, or otherwise shaped.

Unlike the implement 100, the conductive protrusions 304 of the implement 300 are all like-charged. For example, all may be positively charged or all may be negatively charged. In the illustration of FIG. 3, each of the conductive protrusions 304 is illustrated as being positively charged. In this arrangement, an electrical field may not be formed between protrusions, as in the embodiment described above. Instead, a different portion of the implement 300 is charged differently from the protrusions to provide an electrical field. For example, in FIG. 3, the implement 300 includes a conductive element 310, which is illustrated as being negatively charged. The conductive element 310 is illustrated as being a part of the surface 308. In various implementations, the conductive element 310 may be disposed on the surface (either exposed to the atmosphere or inside the housing 302), the conductive element 310 may be embedded in the housing 302 proximate the surface 308, or the surface 308 may be the conductive element 310. Although not illustrated, the conductive element 310 is electrically connected to a power source to be charged. The conductive element may be associated with elements other than or in addition to the surface 308 in other embodiments. For example, the conductive element 310 may be included in additional or alternative sections or surfaces of the housing 302. Moreover, when the housing 302 is embodied as a toothbrush, conductive elements may be included in the head, the neck, and/or the handle.

The conductive element is connected to a power source, and may be made of any conductive material, including but not limited to the conductive materials described above as being suitable for forming the conductive protrusions. Although the protrusions 304 are illustrated only as being formed on the surface 308, they may be alternatively or additionally formed on other surfaces of the housing 302. This disclosure is not limited to the illustrated arrangement of the protrusions 304. The protrusions 304 may vary in number, may be larger and/or smaller, may be further and/or more closely spaced, and the like.

As in embodiments described above, the implement 300 may provide an electrical field. For example, when the protrusions 304 are positively charged as in FIG. 3 and the conductive element 310 is negatively charged, as in FIG. 3, an electrical field is formed proximate the surface 308 of the housing 302. A field will also be generated if the protrusions 304 were negatively charged and the conductive element 310 is positively charged. The field may be used for its direct benefits or it may be used in connection with an activating agent or substance, which benefits are described in more detail above.

Modifications to the implement 300, including but not limited to the modifications noted above with respect to the implement 100, also are within the scope of this disclosure and will be appreciated by those having ordinary skill in the art, with the benefit of this disclosure.

The present disclosure describes oral care devices that are effective and relatively simple to use. The devices described herein may provide physical and electrical stimulation.

Although example embodiments have been described in language specific to the structural features and/or methodological acts, the claims are not necessarily limited to the specific features or acts described. Rather, the specific features and acts are disclosed as illustrative forms of implementing the example embodiments.

What is claimed is:

1. An oral care implement comprising:
a handle;
a head coupled to the handle;
a power source;
a plurality of conductive protrusions electrically connected to the power source and extending from the head, each of the conductive protrusions comprising a base that is proximate to the head and a distal end opposite the base that is spaced from the head; and
wherein at least one of the conductive protrusions tapers from the base to the distal end thereof;
wherein the plurality of conductive protrusions comprises negatively charged conductive protrusions and positively charged conductive protrusions.

2. The oral care implement of claim 1 wherein each of the conductive protrusions tapers from the base to the distal end thereof.

3. The oral care implement of claim 2 wherein each of the conductive protrusions has a triangular cross-sectional shape.

4. The oral care implement of claim 1 wherein the plurality of conductive protrusions are arranged in a plurality of rows, each of the rows comprising either a plurality of the positively charged conductive protrusions arranged in a spaced apart manner or a plurality of the negatively charged conductive protrusions arranged in a spaced apart manner, and wherein rows of the positively charged conductive protrusions alternate with rows of the negatively charged conductive protrusions in a direction parallel to a longitudinal axis of the head.

5. The oral care implement of claim 1 wherein the head has a front surface and an opposite rear surface, wherein a plurality of tooth cleaning elements extend from the front surface of the head and wherein the plurality of conductive protrusions extend from the rear surface of the head.

6. The oral care implement of claim 5 wherein the plurality of conductive protrusions are arranged on the rear surface of the head in a spaced apart manner and span a majority of a length and width of the rear surface of the head.

7. An oral care implement comprising:
a handle;
a head coupled to the handle and comprising a cavity and an outer surface;
a power source located in the cavity, a first electrical pathway coupled to a positive terminal of the power source and a second electrical pathway coupled to a negative terminal of the power source;
a first set of conductive protrusions coupled to the first electrical pathway and extending from the outer surface of the head; and
a second set of conductive protrusions coupled to the second electrical pathway and extending from the outer surface of the head;
wherein the head extends along a longitudinal axis and wherein the first and second electrical pathways each comprise a plurality of transverse portions arranged in an alternating manner in a direction of the longitudinal axis.

8. The oral care implement of claim 7 further comprising a plurality of the conductive protrusions of the first set coupled to each of the transverse portions of the first electrical pathway and arranged in a spaced apart manner and a plurality of the conductive protrusions of the second set coupled to each of the transverse portions of the second electrical pathway and arranged in a spaced apart manner.

9. The oral care implement of claim 7 wherein the head comprises a front surface and an opposite rear surface, and further comprising an opening in the front surface forming a passageway into the cavity.

10. The oral care implement of claim 9 further comprising:
a head plate, distinct from the head, having a front surface, an opposite rear surface, and a plurality of holes extending through the head plate from the front surface to the rear surface;
a plurality of tooth cleaning elements disposed within the holes of the head plate so that first portions of the tooth cleaning elements extend from the front surface of the head plate and second portions of the tooth cleaning elements extend from the rear surface of the head plate, the second portions of the tooth cleaning elements being melted together to form a layer of plastic adjacent to the rear surface of the head plate; and
wherein the head plate is coupled to the head to close the opening in the front surface of the head.

11. An oral care implement comprising:
a handle;
a head coupled to the handle and comprising a cavity and an outer surface;
a power source located in the cavity, a first electrical pathway coupled to a positive terminal of the power source and a second electrical pathway coupled to a negative terminal of the power source;
a first set of conductive protrusions coupled to the first electrical pathway and extending from the outer surface of the head; and
a second set of conductive protrusions coupled to the second electrical pathway and extending from the outer surface of the head;

wherein the head comprises a front surface and an opposite rear surface, and further comprising an opening in the front surface forming a passageway into the cavity; and wherein each of the conductive protrusions of the first and second sets extends from the rear surface of the head.

12. An oral care implement comprising:
a body comprising a handle and a head;
a power source;
a plurality of conductive protrusions electrically connected to the power source and extending from a surface of the body, the plurality of conductive protrusions generating one or more electric fields; and
control circuitry operably coupled to the power source, wherein the control circuitry is configured to pulse at least one of the one or more electric fields;
wherein each of the plurality of conductive protrusions is like-charged, and further comprising a conductive element forming a portion of the surface of the body, the conductive element having an opposite charge from the plurality of conductive protrusions;
wherein the head comprises a first surface and an opposite second surface, wherein the conductive element forms a portion of the second surface of the head, and wherein the plurality of conductive protrusions extend from the second surface of the head.

13. The oral care implement of claim 12 wherein the control circuitry is further configured to automatically deactivate the one or more electric fields after a predetermined period of time has elapsed with the one or more electric fields activated.

14. The oral care implement of claim 12 wherein the power source supplies power in a range of 1 uV to 6V.

15. The oral care implement of claim 12 further comprising a plurality of tooth cleaning elements extending from the first surface of the head.

16. The oral care implement according to claim 12 wherein each of the plurality of conductive protrusions comprises a base proximate the surface of the body and a distal end spaced from the surface of the body, and wherein each of the plurality of conductive protrusions tapers from the base to the distal end.

* * * * *